United States Patent [19]

Bunce

[11] Patent Number: 5,705,397
[45] Date of Patent: *Jan. 6, 1998

[54] ANALYTICAL DEVICES AND METHODS OF USE

[75] Inventor: Roger Abraham Bunce, Kings Norton, England

[73] Assignee: British Technology Group Limited, London, England

[*] Notice: The term of this patent shall not extend beyond the expiration date of Pat. No. 5,516,488.

[21] Appl. No.: 495,539

[22] PCT Filed: Feb. 23, 1994

[86] PCT No.: PCT/GB94/00356

§ 371 Date: Aug. 25, 1995

§ 102(e) Date: Aug. 25, 1995

[87] PCT Pub. No.: WO94/20215

PCT Pub. Date: Sep. 15, 1994

[30] Foreign Application Priority Data

Mar. 4, 1993 [GB] United Kingdom .................. 9304452

[51] Int. Cl.⁶ .................................................. G01N 31/22
[52] U.S. Cl. .................... 436/180; 422/56; 422/58; 422/61; 436/169
[58] Field of Search .............................. 422/56–58, 61; 436/164, 169, 180

[56] References Cited

U.S. PATENT DOCUMENTS

| | | | |
|---|---|---|---|
| 4,810,470 | 3/1989 | Burkhardt et al. | 422/58 |
| 5,177,021 | 1/1993 | Kondo | 422/58 |
| 5,198,193 | 3/1993 | Bunce et al. | 422/58 |
| 5,202,268 | 4/1993 | Kuhn et al. | 422/58 |
| 5,354,538 | 10/1994 | Bunce et al. | 422/58 |
| 5,516,488 | 5/1996 | Bunce et al. | 422/56 |

FOREIGN PATENT DOCUMENTS

| | | |
|---|---|---|
| 0 262 328 | 4/1988 | European Pat. Off. . |
| 2 261 284 | 5/1993 | United Kingdom . |
| WO 89/03992 | 5/1989 | WIPO . |
| WO 90/11519 | 10/1990 | WIPO . |

Primary Examiner—Lyle A. Alexander
Attorney, Agent, or Firm—Nixon & Vanderhye

[57] ABSTRACT

An analytical device (1) for use in assay procedures comprises at least one liquid flow channel of porous material leading from a channel end to an analytical site (2) via a localized reagent site (3). A liquid-impermeable barrier (6) is arranged adjacent to the reagent site (3) in the liquid flowpath to slow the transport of the reagent to the analytical site (2) by creating a substantially stagnant zone (10) which has the effect of elongating the distribution of reagent in the liquid flow.

17 Claims, 1 Drawing Sheet

ANALYTICAL DEVICES AND METHODS OF USE

BACKGROUND OF THE INVENTION

This application is the national filing of PCT/GB94/00356, filed Feb. 23, 1994.

The invention concerns analytical devices for use in assay procedures.

Simple self-contained devices for performing biochemical diagnostic assays in extra-laboratory conditions are being used in an ever widening range of applications. These devices are designed to avoid the need for complex manual procedures such that they can be reliably carried out by an unqualified user.

The analysis to be carried out in such assay procedures is generally in respect of an analyte in the form of an antigen within a body fluid sample, such as a sample of blood or urine. Generally, the antigen will first be specifically bound with antibody held at an analytical site. A first reagent, for example a labelling reagent, is then delivered to the analytical site, followed by a second reagent, for example a label detection reagent to provide a signal for the user. The signal may for example be a colorimetric change, the colour or intensity of colour produced providing information for the user.

Devices for realising an assay procedure of this kind are disclosed in patent application Ser. No. WO-90/11519, in which first and second liquid flow channels of porous materials end from a respective pair of channel ends to a common site, the channels being operable to transfer liquid by capillary flow to the common site in sequentially timed manner following simultaneous application of the liquid to the pair of channel ends. Document EP-A-0262328 describes a test strip for biochemical analysis, including an embodiment comprising multiple solvent transport pathways. One of the pathways may feature a convoluted flow-path formed by the incorporation of baffles in the device.

The first and second reagents are delivered to the analytical site by a liquid, such as a buffer solution. This solubilises and entrains the reagents to carry them onwards and thereby deliver them to the analytical site. The speed at which a reagent is carried is dependent on the length of the column of liquid, and a typical relationship may be represented as follows:

$$T = kL^n$$

where T=time of travel, L=length of liquid column, and, for a constant width of channel, k and n are positive constants specific to the material of the device. For example, for Millipore AP25 filter paper, if T is in seconds and L is in min., k=0.016 and n=2.1.

Because the column of liquid carrying the first reagent through the analytical site is shorter than that subsequently carrying the second reagent through the analytical site, the first reagent travels considerably faster than the second (see the equation above). In sequential delivery analytical devices of this sort, whilst the second reagent is an enzymic reagent (which is often provided in excess), the first reagent is usually involved in an antibody/antigen reaction. For such a reaction it is most important that the time of contact between the reagents, or incubation period, is sufficient. With currently available devices this is not always the case and there is therefore a need to improve the effectiveness of this incubation stage.

The need to provide a sufficient incubation period is not of course restricted solely to sequential delivery analytical devices featuring two or more reagents, but can arise more generally with liquid transfer analytical devices.

SUMMARY OF THE INVENTION

It is an object of this invention to improve the situation described above and to this end there is provided an analytical device for use in assay procedures, comprising at least one liquid flow channel of porous material for capillary flow therealong, the channel leading from a channel end to an analytical site via a localised reagent site so as to provide a flow path to transport liquid from the channel end through the reagent site, wherein a permanent liquid-impermeable barrier is provided adjacent to the reagent site, the barrier intercepting said flow path to create a substantially stagnant zone whereby the distribution of the reagent is elongated as it is delivered from the reagent site to the analytical site by entrainment in said capillary flow.

The liquid-impermeable barrier is arranged in such a way that it provides an obstacle to the transport of a reagent from the reagent site and therefore slows the transport of the reagent relative to the overall rate of transport of the liquid.

The liquid-impermeable barrier is preferably located on the upstream side of the reagent site, but for certain applications may be on the downstream side.

Different forms of barrier are envisaged, the flow characteristics within the flow channel depending on the form selected.

In another aspect of the invention there is provided a method of controlling the rate of delivery of a reagent to an analytical site, said method comprising:

providing at least one porous liquid flow channel in which said analytical site is located, the flow channel having a channel end and incorporating a localised reagent site, and having a permanent liquid impermeable barrier positioned adjacent to the reagent site;

providing a selected reagent at the reagent site;

introducing liquid to said channel end to initiate capillary liquid flow along the flow channel to the analytical site via the reagent site, the impermeable barrier creating a substantially stagnant zone, and the site relationship between the impermeable barrier and the reagent site being such that the relatively stagnant zone results in elongation of the distribution of the reagent as it is delivered to the analytical site by entrainment in said capillary flow.

The method may also include controlling the form of the relatively stagnant zone by selecting the flow characteristics within the flow channel.

The device and method according to the invention provide elongation of the flow of solubilised reagent such as to extend the incubation period for file reaction between the reagent and analyte at the analytical site. The incubation period can be varied as required by selecting an appropriate form of barrier.

BRIEF DESCRIPTION OF THE DRAWINGS

Certain embodiments of tho invention will now be described by way of example with reference to the accompanying drawings, in which.

DETAILED DESCRIPTION OF THE PREFERRED EMBODIMENTS

Figure 1:
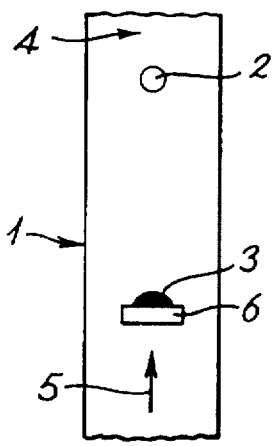
FIG. 1 schematically illustrates one embodiment of an analytical device according to the invention.

In FIG. 1 an analytical test strip is represented by reference 1. This is formed from a sheet of porous material appropriate for capillary liquid flow and a material such as that supplied under the trade name Millipore AP25 is suitable for such application. The test strip shown features a single liquid flow channel in which there is an analytical site 2 where an analyte can be immobilised. The analyte is, for example, an antigen within a sample of body fluid such as blood or urine. The antigen is immoblised by being specifically bound with antibody held at the analytical site. The test strip has a reagent site 3 where a reagent is impregnated into a specific zone in the porous material.

It will be appreciated that the test strip may feature a plurality of channels, a plurality of reagent sites, and/or even a plurality of analytical sites within the same device. Only a single reagent site 3 and a single analytical site 2 are represented in FIG. 1 to illustrate the invention. Moreover the test strip need not be of simple sheet form but may be, for example, of multi-layer construction.

In use, a liquid, such as an appropriate buffer solution, is introduced to an end of the test strip 1 such that capillary action causes it to flow along the strip in the direction of the arrow 5 in FIG. 1. When the liquid reaches the reagent site 3 the reagent is solubilised and entrained such that it is carried by the channel flow towards the analytical site 2. As the reagent is carried through the analytical site the reaction between the reagent and the antibody-bound antigen takes place. The flow continues washing unbound serum and any other waste material onwards to downstream area 4 which serves as a waste reservoir.

A further step may then take place wherein a second reagent is carried to the analytical site. As mentioned above, this sequential delivery of reagents to the analytical site can be realised by a single test strip featuring multiple flow channels determining the relative times of delivery to the analytical site.

Figure 2:
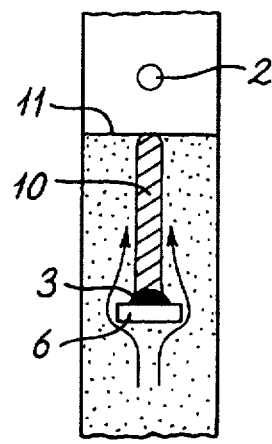
FIG. 2 illustrates the operation of the device or FIG. 1.

FIG. 1 also shows a liquid-impermeable barrier 6 in the form of a rectangular zone, or bar, extending at right angles to the direction of liquid flow and arranged centrally of the strip and immediately upstream of the reagent site 3. As shown in FIG. 2, the liquid flow approaches the barrier 6 and then separates around its edges, the reagent site being located in the wake of the barrier. The result of this Is that there is produced a substantilly stagnant zone downstream of the barrier. The liquid will gradually flow into this zone to solubilise and entrain the reagent in the direction of the analytical site, but the reagent will be carried at a slower speed than that of the advancing flow front 11 of the liquid and effectively the moving reagent will be elongated as shown by reference 10. This has the effect of extending the time of contact, or incubation period, between the reagent and the antibody-bound antigen. As explained above, the incubation period of this reaction is very important in obtaining an effective analytical result. As a result of this feature, the sensitivity of the test strip is increased. The reagent site may be directly adjacent or abutting the liquid-impermeable barrier 6, or may be located at a short distance from the barrier, and the separation between the two influences the degree of elongation of the entrained reagent. The closer they are together, the more will be the elongation.

Although liquid-impermeable barrier 6 forms an obstruction to the flow of any subsequent reagent carried along the test strip, the initial liquid flow establishes two streambands, one on either side of the barrier, which rejoin one another beyond the barrier. Any solubilised reagent carried along the test strip therefore flows past the substantially stagnant zone and merges again beyond the barrier, without being slowed in the same way as the flow of the first reagent. Similarly, if the flow in the test strip is reversed, as is the case in certain analytical devices, any reagent will flow around the sides of the barrier and rejoin on the other side.

Figure 3:
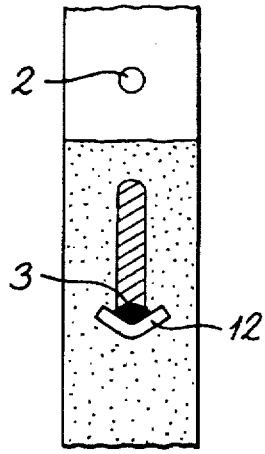
FIGS. 3–6 illustrate further embodiments of the device according to the invention.

FIG. 3 shows an alternative embodiment of a device according to the invention. The liquid-impermeable barrier takes the form of a shallow 'V' 12, the apex of the 'V' being directed upstream and the reagent site 3 being located between the arms of the 'V'. This has the effect of increasing the elongation of the entrained reagent and can provide an initial wash at the analytical site 2 to remove unfixed material from the site before delivery of the reagent to the site commences. Conversely, an inverted 'V' shaped liquid-impermeable barrier reduces elongation and wash.

Figure 4:
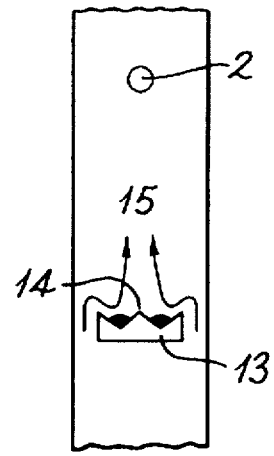

In the 'V' form barrier as shown in FIG. 3, when the reagent site 3 is located in the hollow of the 'V' between the arms there may be produced a wholly stagnant region at this point, resulting in some of the reagent being entrapped therein, either completely or at least for an unacceptable length of time. To avoid this undesirable situation a form of barrier as shown in FIG. 4 can be used, featuring a rectangular barrier 13 with two 'V'-form recesses on the downstream side of the barrier and two reagent sites, one in the hollow of each of the recesses. Liquid under capillary action flows around both sides of the barrier and down into the recesses, entraining the reagent and carrying it onwards to the downstream apex 14 between the two 'V'-form recesses where the liquid stream bands rejoin one another. Because the liquid flow 15 sweeps through the hollow of the V-form recesses there is no danger of forming an unwanted stagnation region therein.

For some chemical assays it s necessary to mix two reagents shortly before delivering the reaction product to the analytical site. The design of barrier shown in FIG. 4 is very effective for such a technique, as each of the two 'V'-form recesses may contain a different reagent, kept apart on the test strip until the two liquid stream bands respectively entrain the two reagents and bring them together at the point where the liquid stream bands join one another, before the common flow carries the reaction product downstream towards the analytical site 2. For example, the manufacturer of the device could apply a reagent to one reagent site, the user would apply a sample to the other reagent site, and in use the user would apply the diluent at the channel end to cause sample and reagent to mix and elongate in travelling towards the analytical site.

Figure 5:
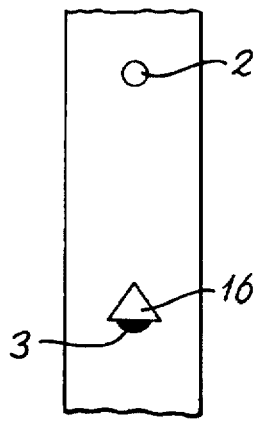

FIG. 5 illustrates yet another embodiment of a device according to the invention. The liquid-impermeable barrier in this case is of triangular form 16 with an apex directed downstream and with the reagent site 3 being located on the upstream side of and adjacent to the barrier. The flow of the solubilised first reagent is still elongated as it has to take a longer route around the barrier than the advancing front of the liquid flow. The triangular form of the barrier encourages the two streambands on either side to rejoin downstream of the barrier as quickly as possible, both in the case of the solubilised first reagent and in that of subsequently delivered reagents.

Figure 6:
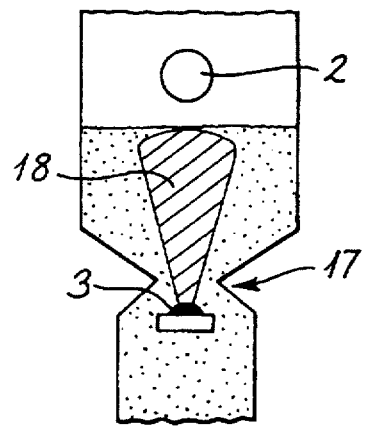

One result of the elongation of the solubilised reagent may be the narrowing of its flowpath. If it narrows such that it becomes narrower than the analytical site the positive result in the case of a subsequent colour change may be indicated by a thin line rather than a comprehensive colour change at the analytical site. To avoid this, the width of the flowpath of the reagent may be increased immediately downstream of the reagent site to widen the elongated reagent flow. Alternatively a necked section 17 of the porous channel in the region of or just downstream of the liquid-impermeable barrier may be provided, as shown in FIG. 6. The narrowing of the porous channel at this necked section 17 results in a widening elongated reagent flow 18. By careful selection of the channel geometry the flow pattern and hence the concentration of reagent can be controlled.

Clearly yet further forms or arrangements of liquid-impermeable barriers other than those described above are possible, the specific design being selected as appropriate to vary the incubation period and generally to influence the flow of the reagent as desired. A plurality of liquid-impermeable barriers may also be used.

The liquid-impermeable barrier may be formed by excision or omission of material as a stage in the manufacturing of the test strip, for example, by stamping. Alternatively, an agent, such as wax, can be applied to the strip to render it impermeable in the appropriate region. The barrier may be physically or chemically etched on to the strip, for example by laser etching techniques.

Embodiments of the invention illustrated n the accompanying Figures and described above are given by way of example only, and it should be understood that these n no way limit the scope of the invention, which is intended to embrace all embodiments that fall within the spirit and scope of the appended claims.

I claim:

1. An analytical device for use in assay procedures, comprising at least one liquid flow channel of porous material for capillary liquid flow therealong, the channel having:
   a channel end for liquid application thereto,
   an analytical site, said channel defining a liquid flow path leading in a downstream direction from said channel end to said analytical site,
   a localized reagent site said channel end and said analytical site, and
   a permanent liquid impermeable barrier in said channel between said channel end and said analytical site, said barrier being constructed and adapted to create a substantially stagnant zone by intercepting said liquid flow path and extending partially across the channel width, sufficiently close to said localized reagent site that, on application of a reagent to said localized reagent site and application of liquid to said channel end, said substantially stagnant zone is created whereby the distribution of said reagent is elongated as it is delivered from said reagent site to said analytical site by entrainment in said capillary flow.

2. An analytical device according to claim 1, wherein said liquid-impermeable barrier is provided by application of an agent to render the porous material impermeable in a selected region.

3. An analytical device according to claim 1, wherein said liquid-impermeable barrier is provided by absence of porous material in a selected region.

4. An analytical device according to claim 1, wherein said liquid-impermeable barrier is on the upstream side of the reagent site.

5. An analytical device according to claim 1, wherein said liquid-impermeable barrier is on the downstream side of the reagent site.

6. An analytical device according to claim 1, wherein said liquid-impermeable barrier is shaped as a rectangular bar arranged substantially perpendicularly across the liquid flow path.

7. an analytical device according to claim 1, wherein said liquid impermeable barrier is substantially V-shaped.

8. An analytical device according to claim 7, wherein the arms of the V-shaped liquid-impermeable barrier extend on either side of the reagent site in a downstream direction.

9. An analytical device according to claim 1, wherein said liquid impermeable barrier features two V-shaped recesses on its downstream side.

10. An analytical device according to claim 9, wherein a different reagent is placed within each of the V-shaped recesses.

11. An analytical device according to claim 1, wherein said liquid impermeable barrier includes two sides which converge to meet at a point at its downstream end.

12. An analytical device according to claim 1, wherein said liquid flow channel features a variation in channel width in the region of the reagent site.

13. An analytical device according to claim 12, wherein the variation is a narrowed portion in the channel.

14. A method of controlling the rate of delivery of a reagent to an analytical site in an assay procedure, said method comprising:
   providing at least one porous liquid flow channel in which an analytical site is located, said channel also having a channel end for liquid application thereto, and incorporating a localized reagent site, said channel also having a permanent liquid impermeable barrier between the channel end and said analytical site, said barrier extending partially across the width of said channel;
   providing a selected reagent at the reagent site;
   introducing liquid to said channel end to initiate capillary liquid flow along the flow channel to the analytical site via the reagent site, the impermeable barrier creating a substantially stagnant zone, said impermeable barrier being sufficiently close to the reagent site such that the substantially stagnant zone results in a slowing of transport of the reagent relative to transport of said liquid as it is delivered to the analytical site by entrainment in said capillary flow.

15. A method according to claim 14, whereby the form of the relatively stagnant zone is controlled by selecting the flow characteristics within the flow channel.

16. A method according to claim 15, whereby selected flow characteristics are determined by varying the width of the flow channel.

17. An analytical device for use in assay procedures, comprising at least one liquid flow channel of porous material for capillary liquid flow therealong, the channel having:
   a channel end for liquid application thereto,
   an analytical site, the channel defining a liquid flow path leading in a downstream direction from said channel end to said analytical site,
   a localized reagent site in said liquid flow path between said channel end and said analytical site, and
   permanent liquid impermeable barrier means between said channel end and said analytical site and extending partially across the channel width for intercepting said liquid flow path on application of a reagent to said localized reagent site and application of liquid to said channel end, said barrier means being constructed and adapted to create a substantially stagnant zone, whereby transport of said reagent from said reagent site to said analytical site is slowed relative to transport of said liquid.

* * * * *